(12) United States Patent
Tiedtke et al.

(10) Patent No.: US 7,175,605 B2
(45) Date of Patent: Feb. 13, 2007

(54) THERAPEUTIC CATHETER HAVING SENSOR FOR MONITORING DISTAL ENVIRONMENT

(75) Inventors: Hans Jurgen Tiedtke, Aachen (DE); Horst Lussem, Duren (DE)

(73) Assignee: Convergenza AG, Furstentum (LI)

( * ) Notice: Subject to any disclaimer, the term of this patent is extended or adjusted under 35 U.S.C. 154(b) by 164 days.

(21) Appl. No.: 10/753,133

(22) Filed: Jan. 6, 2004

(65) Prior Publication Data

US 2004/0153109 A1 Aug. 5, 2004

Related U.S. Application Data

(63) Continuation of application No. 09/030,499, filed on Feb. 25, 1998, now Pat. No. 6,689,089.

(30) Foreign Application Priority Data

Apr. 26, 1997 (DE) .................... 197 17 790

(51) Int. Cl.
*A61M 1/00* (2006.01)
*A61M 3/00* (2006.01)
(52) U.S. Cl. ............... 604/27; 604/35; 604/43; 606/159
(58) Field of Classification Search ............ 604/22, 604/27, 36, 35, 43; 606/159, 170, 180
See application file for complete search history.

(56) References Cited

U.S. PATENT DOCUMENTS

| | | | |
|---|---|---|---|
| 4,850,972 A | 7/1989 | Schulman et al. | |
| 4,895,560 A | 1/1990 | Papantonakos | |
| 5,308,354 A * | 5/1994 | Zacca et al. | 606/159 |
| 5,496,267 A | 3/1996 | Drasler et al. | |
| 5,501,694 A | 3/1996 | Ressemann et al. | |
| 5,536,242 A | 7/1996 | Willard et al. | |
| 5,733,256 A | 3/1998 | Costin | |
| 5,788,667 A | 8/1998 | Stoller | |
| 5,795,325 A * | 8/1998 | Valley et al. | 604/509 |
| 5,941,869 A | 8/1999 | Patterson et al. | |
| 6,001,112 A * | 12/1999 | Taylor | 606/159 |

* cited by examiner

*Primary Examiner*—Catherine S. Williams
(74) *Attorney, Agent, or Firm*—Crompton, Seager & Tufte LLC

(57) ABSTRACT

Apparatus with a pneumatic or hydraulic or mechanical therapeutic catheter. The therapy energy required to treat internal vessels of the patient is transferred by the same fluid or the same elements from the proximal end section to the distal end section of the catheter that transfer information from the distal end section to the proximal end section of the catheter. The information provides understanding of the estate of the vessel and how the therapy fluid of the therapy element of the catheter acts on the vessel.

12 Claims, 2 Drawing Sheets

THERAPEUTIC CATHETER HAVING SENSOR FOR MONITORING DISTAL ENVIRONMENT

This Application is a continuation of application Ser. No. 09/030,499, filed Feb. 25, 1998, now U.S. Pat. No. 6,689,089.

BACKGROUND OF THE INVENTION

The present invention concerns generally a medical device. More specifically, the present invention concerns a therapeutic catheter for treatment of vessels in a patient. The present invention includes catheters having proximal sensors for measuring changes at the distal end of the catheter.

DESCRIPTION OF RELATED ART

A therapeutic catheter having at last two channels or lumens extending through it in the longitudinal direction is known from EP-A-0 527 312 (corresponds to DE 41 26 886 A1). One lumen is a flow channel to supply liquid with high pressure (for example, 75 bar), from the near or proximal end to the far or distal end of the catheter. The catheter has an open flow path on its distal end at which the liquid in the form of a sharp jet can separate parts of a body tissue in a patient and convey them into the other lumen, which serves as return channel and transports the liquid together with the separated tissue material to the proximal end of the catheter. A similar or therapeutic catheter is also known from the published Patent Application DE 42 01 992 A1. Other known therapeutic catheters, like the one known from U.S. Pat. No. 5,380,273, have one or even two expansion elements, so-called dilation balloons, on the distal end with which blood vessels in a patient can be dilated or blocked. Moreover, mechanical catheters with a rotating tool on their distal end section to remove material in vessels of a patient are known from U.S. Pat. No. 5,092,872 and the unexamined German Applications DE 38 01 318 A1, DE 38 28 478 A1 and DE 43 23 756 A1. PCT-WO 89/09029 also exhibits a mechanical catheter with pivotable tools on the distal catheter end.

During introduction of a catheter into a patient the physician can observe the position of the catheter on an x-ray screen. However, the tissue or condition of the tissue is not recognizable or not clearly recognizable on the x-ray screen. The physician is therefore not capable of checking the therapeutic success on-line during therapy. He receives no feedback as to whether a vascular obstruction, for example, has been sufficiently eliminated. He is forced to adopt an iterative procedure "therapy, control, therapy, and so forth" in which the physician must rely on his experience and feelings in establishing the control intervals. This procedure leads to frequent control angiographies which expose the patient to radiation and contrast agents.

To summarize, this means that, when therapeutic catheters of the aforementioned types are used combined with x-ray imaging devices, the user only receives information concerning the position of the catheter in the patient, but the actual therapeutic function is not visible.

A hydrodynamic thrombectomy catheter in which fluid is guided via a channel system to treat the patient tissue and ultrasound is guided via a separate system to the tip of the catheter for optical monitoring of catheter operation is known from EP 0 483 133 A1. The therapy channel for the fluid and the diagnosis channel for the ultrasound diagnosis are separate and independent of each other.

In catheters in which laser radiation or ultrasound is used to treat patient tissue, the function of the catheter tip in a patient tissue can be monitored simply by reflecting laser beams or ultrasound waves. Such catheters are known, for example, from the following documents: publication of the article "Laser-induced Shockwave Lithotripsy with Microsecond Laser Pulses" in the journal *Laser und Optoelektronik* 20(4)/1988 by R. Engelhardt, W. Meyer, S. Thomas, P. Oehlert; published Patent Applications DE 43 22 955 A1 and DE 195 22 310 A1; Patent DE 42 40 182 C2, U.S. Pat. No. 5,104,392 and EP 0 582 766 A1. Moreover, a therapeutic catheter for treatment of patent tissue with laser light having an additional internal hollow channel to which a laser beam is transmitted for diagnostic purposes is known from DE 44 37 578 A1. Several therapeutic catheters are also known from EP 0 629 380 A1: a catheter for elimination of stenoses by laser radiation, a catheter with an expandable balloon on the distal end of the catheter to eliminate stenoses, and a catheter to treat patient vessels with ultraviolet light to prevent new formation of stenoses in blood vessels of the patient. No diagnostic possibilities are provided in these last-named catheters.

SUMMARY OF THE INVENTION

The invention is supposed to solve the task of devising a possibility in catheters having fluid channels and/or mechanical tools for therapeutic treatment of patient vessels, through which a signal can be generated in simple fashion, providing the user with information concerning the therapeutic effect of his work with the catheter in a patient.

Catheters according to the present invention can include a fluid channel extending at least from the proximal end to the distal end, and in some embodiments, return from the distal end to the proximal end. External changes in environment of the fluid in the distal end section of the catheter can cause one or more physical values or value changes to the fluid. The value changes can be measured at the proximal end of the catheter.

In one aspect of the invention, sensors or measurement devices on the proximal section of the catheter can measure physical changes in the fluid which are caused by external conditions acting on the fluid in the distal section of the catheter. In one embodiment, the distal section has an expandable element such as an inflatable balloon which can be inflated by fluid in the fluid channel. Sound or pressure can be measured at the proximal end of the catheter. In another embodiment of the invention, the distal section can include an open portion having hydrodynamic jet which can be used to break up a vessel occlusion and sweep broken pieces proximally through the fluid channel. Sound or pressure changes in the fluid caused by changes at the distal end can be measured at the proximal end. In yet another embodiment, a rotating tool at the distal end can be driven by a rotating shaft extending from the distal end to the proximal end. Changes in torque at the proximal end can be measured. The proximally measured changes can be output as optically or acoustically recognizable signals or values. Some embodiments have an acoustic signal generator for converting the detected or measured values into acoustic signals audible to persons.

The fundamental idea of the invention is as follows: when therapeutic catheters are used in which the energy is transported in the form of a liquid or gaseous fluid under pressure or in the form of mechanical energy from the proximal end section to the distal end section, especially to the catheter tip of the catheter and used there for therapy in a patient, the energy is altered by feedback from the patient tissue. Or in other words, the magnitude and type of energy released at the catheter tip to the surroundings is changed by feedback from these surroundings to this energy. In a gaseous or liquid fluid under pressure for removal of material in patient vessels, the pressure of the fluid is changed as a function of the flow resistance of the fluid between the distal end section of the catheter and its surroundings, which is formed by the patient tissue.

Noise also develops in the fluid stream and thus sound waves as a function of whether the fluid encounters patient tissue and/or ablates the patient tissue and/or the ablated or cut patient tissue is drawn by the fluid into the fluid channel. These pressure changes and/or noise or sound waves occurring on the distal end section of the catheter are determined according to the invention on the proximal end section of the catheter by a sensor or measurement device and made acoustically audible [sic] or visually visible [sic] for an operating person of the catheter. Because of this the operating person with reference to this acoustic or optical signal can recognize whether the fluid and in which way the fluid is acting on a patient tissue in a patient. In similar fashion the torque and/or noise developments of a drive shaft, which drives a rotating tool on the distal end of the catheter, are measured by the invention during use of mechanical catheters in the therapeutic treatment of patient vessels. An acoustic and/or visible signal or measurement result is generated as just described from these measurements, with reference to which an operating person can recognize and evaluate the effect of the rotating tool on a patient vessel in a patient. These changes in energy in the form of pressure changes, sound generation or sound changes or torque and torque changes which occur on the distal end section of the catheter, are determined or measured by the invention on the proximal end section of the catheter, during which this measurement is conducted in the same fluid or in the same mechanical element on the proximal end section of the catheter that conveys the energy to the distal end section of the catheter. Thus, according to the invention, the same channel and the same fluid or the same mechanical element is used for therapy of the patient as for signal production. By connecting a sensor or measurement element to the fluid channel or the mechanical drive element on the proximal end section of the catheter the aforementioned changes are recorded and made visible and/or audible to the user. The treatment medium "fluid" or "drive element" thus has a dual function, in which it serves both for therapy and energy transmission from the proximal end section to the distal end section of the catheter and in the opposite direction as an information path from the distal end section to the proximal end section of the catheter. No information path in addition to the therapy path is required for information transmission.

Additional features of the invention are contained in the subclaims.

BRIEF DESCRIPTION OF THE DRAWINGS

The invention is described below with reference to the drawings of preferred variance. In the drawings FIG. 1 schematically depicts a device with a balloon catheter for therapeutic treatment, FIG. 2 schematically depicts a device with a mechanical catheter with a rotating shaft, FIG. 3 schematically depicts a device with a high-pressure fluid catheter for removal of vessel parts in a patient with acoustic and optical means of indication for pressure and/or sound and/or flow rate of the fluid in the catheter.

DETAILED DESCRIPTION OF THE INVENTION

Figure 1:
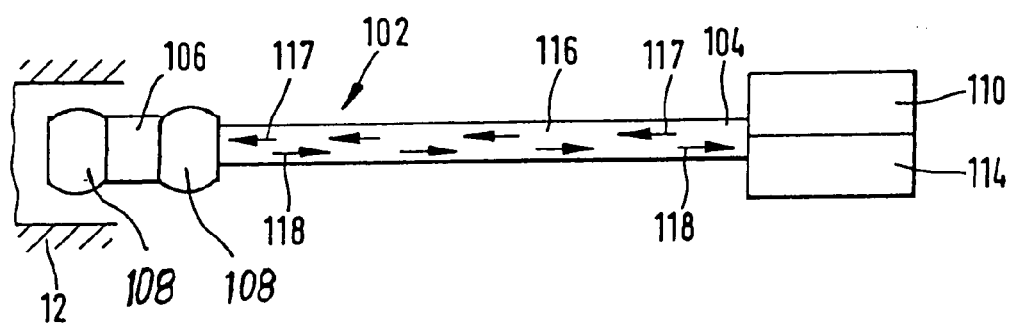
Figure 2:
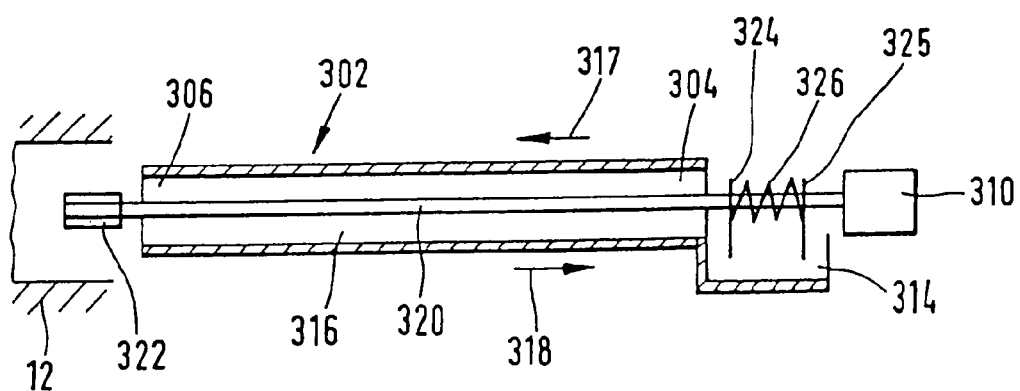
Figure 3:
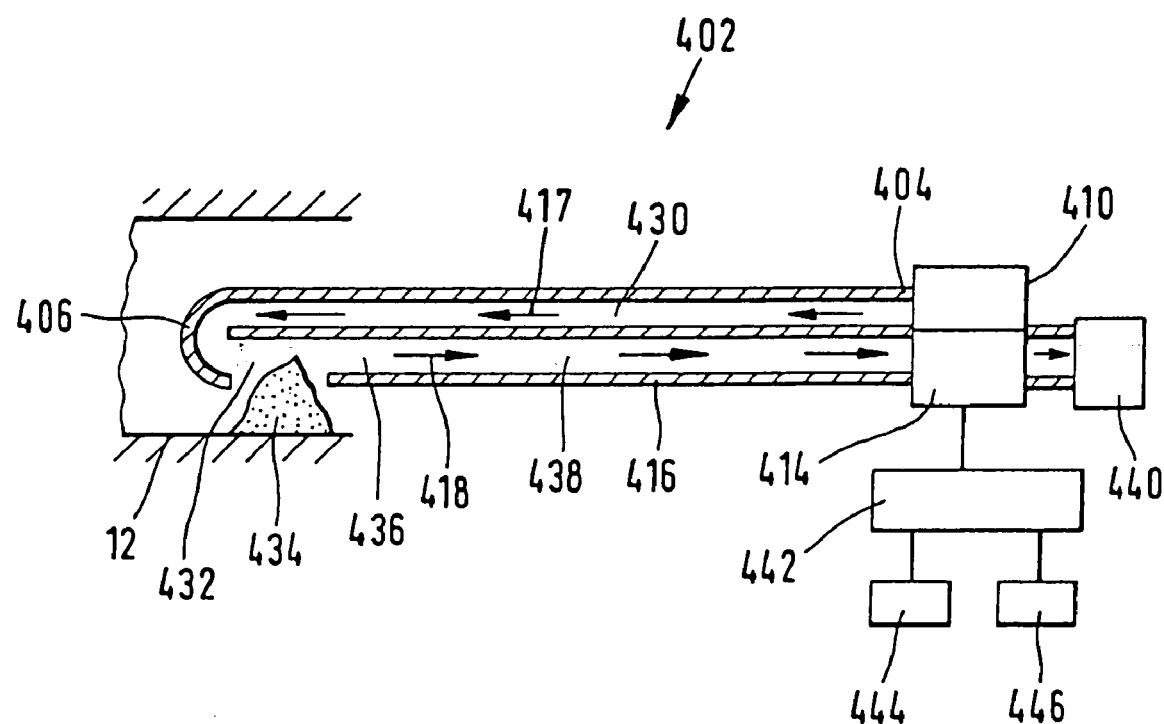

The invention concerns therapeutic catheter a) according to FIG. 1 in the form of balloon catheters (PTA, PTCA) with one or more expandable balloons on the distal end section, in which the measurable form of energy is the pressure and/or volume of a liquid or gas; b) according to FIG. 2 in the form of mechanical catheters whose measurable form of energy is the torque of a rotating tool or a rotating shaft, or changes of this form of energy in the form of sound waves that are generated in mechanical rotating objects during interaction with a patient vessel; c) according to FIG. 3 in the form of hydrodynamic catheters whose measurable form of energy is the kinetic energy and/or the flow rate of the fluid and/or the noise development in the fluid during flow through the catheter, in which the fluid can be liquid or gas.

FIG. 1 schematically depicts a device with a balloon catheter 102, which has a proximal end section 104 and a distal end section 106. The distal end section 106 has one or more radially expandable balloons 108 arranged axially in sequence with which blood vessels can be blocked or narrowed blood vessels 12 widened. For this purpose the corresponding balloon 108 can be expanded with fluid from a fluid source 110 mounted on the proximal end section 104, which can be a liquid or gas, which flows through at least one therapy and information channel 116 of catheter 102. For this purpose a fluid is conveyed at a predetermined volume or pressure of the fluid source 110 into the corresponding balloon 108. The fluid source can be a hand-operated piston-cylinder unit or a syringe. The pressure required to fill balloon 108 with a predetermined volume depends on the condition, especially the opening cross section, of the blood vessel 12 to be expanded. In a severely constricted blood vessel 12 a much greater pressure is required to fill the corresponding balloon 108 with a predetermined volume than in an unconstricted or only slightly constricted blood vessel 12. The time trend of volume and the time trend of pressure during filling of the balloon or balloons 108 can be detected or measured by sensors or means of measurement 114 on the proximal end section 104 of catheter 102 and provide an experienced operating person with acoustic and/or optical information concerning the position and effect of the balloon 108 in blood vessel 12 and concerning the state of blood vessel 12. The operating person knows the values of a healthy and normal vessel of a comparable person in comparison with these detected or measured values or, if the patient is an animal, of a comparable animal. During filling of the balloon or balloons 108 the fluid flows through channel 116 in direction 117 to the distal end section 106, whereas during emptying of balloons 108 the fluid flows in the opposite direction 118 through the same (or another) channel 116 to the proximal end section 104 back to the fluid source 110 or to a means of ventilation or storage.

FIG. 2 schematically depicts a device with a mechanical catheter 302 provided with a rotatable shaft extending through it lengthwise. Such mechanical catheters 302 are used, in particular, but not only for thrombectomy and arthrectomy. The shaft 320 is driven by a motor 310 on the proximal end section 304 so that a tool 322 fastened on its distal end can process vascular material on the distal end section 306 of the catheter in a vessel 12 of a patient, for example, ablate, fragment or destroy it. The ablated or fragmented vascular material can remain in the patient or be conveyed by appropriate means to the proximal end section 304. The torque of shaft 320 depends on how great the resistance of vessel 12 is in the patient to the tool 322 on the distal end of the shaft. The corresponding torque and torque changes of shaft 320 can be measured by a torque sensor 314 on the proximal end section 304 of the catheter. This means that the shaft 320 transmits information from the distal end section 306 to the proximal end section 304 in the form of torque or torque changes, which are measured by torque sensor 314 and optically and/or acoustically displayed. The torque can be displayed as torque or in other measurement units which are a gauge for the operating person of the condition of vessel 12 and the activity of tool 322 in this vessel 12. The torque sensor 314 can have two angle sensors 324 and 325 arranged on shaft 320 and a torsion spring 326 arranged between them and attached to them, with which the torque transferred by shaft 320 and thus the torque changes can be measured. The energy transmission for therapy of the patient also occurs here through the same element, namely through shaft 320, from the proximal end section 304 to the distal end section 306 of catheter 302 according to arrow 317 and the information flow concerning the condition of the vessel 12 and the type and scope of the effect of tool 322 on the vessel 12 occurs in the opposite direction according to arrows 318 through the same shaft 320 from the distal end section 306 to the proximal end section 304. The shaft 320 thus has the function of both a therapeutic element and an information transmission element.

FIG. 3 shows an apparatus with a hydrodynamic catheter 402 for therapeutic treatment of a vessel 12 in a patient with a gaseous or preferably liquid fluid under pressure. The catheter 402 contains a fluid path consisting of a flow channel 430, a path section 432 open to the outside surroundings on the distal end section 406 of the catheter and a return channel 438. A pressurized fluid source 410 can convey a pressurized fluid, for example, gas or preferably liquid at very high pressure of, say, 75 bar, on the proximal end section 404 of catheter 402 into the flow channel 430 in the direction of arrow 417. The pressurized fluid arrives at the distal end section 406 of catheter 402 in the form of a sharp fluid jet in the open path section 432, treats the vessel 12 there, for example, cuts or fragments the vascular constriction material 434 and then flows into the distal end 436 of the return channel 438 with entrainment of material 434 and then through the latter in the direction of arrow 418 to the proximal end section 404 to a container 440. A pressure sensor 414 with a defined hydraulic resistance is connected on the proximal end section 404 of return channel 436. The pressure sensor 414 measures the pressure drop over the hydraulic resistance. The measured pressure varies as a function of flow resistance of the fluid in the flow path of the catheter, for example, the size of the vascular constriction 434, and as a function of whether and how much material 434 and possibly blood is conveyed by the pressurized fluid from the vessel 12 of the patient in the return channel 438. The pressure measured by pressure sensor 414 on the proximal end section 404 in return channel 438 is therefore information concerning whether and how the pressurized fluid acts on vessel 12 and what the state of vessel 12 is and whether the pressurized fluid stream is transporting much, little or no vascular constriction material 434, and also information concerning how the distal end section 406 is positioned relative to the location 434 of vessel 12 being treated. The same pressurized fluid therefore transmits via the same fluid path 430, 432, 438, both the energy for therapy of vessel 12 and also information for the person using the catheter 402.

The pressure sensor 414 of FIG. 3 is connected via an electronic signal evaluation circuit 442 to an optical display device 444 and/or to an acoustic signal generator 446, especially an earphone or loudspeaker. The optical display device 444 shows the user of catheter 402 the aforementioned information. The acoustic signal generator 446 generates tones or noises that the user can hear, depending on the information.

The electronic evaluation circuit 442, the optical display device 444 and the acoustic signal generator 446 can also be used in combination with sensors 114 and 314 of the other FIGS. 1 and 2 in order to convert their signals into an optical display signal and/or an acoustic indication signal.

In the variants according to FIGS. 1 and 3 the fluid can be passed through several channels in parallel instead of through one channel.

Noises develop in the pressurized fluid with a catheter 102 of FIG. 1 and catheter 402 of FIG. 3 as a function of whether the pressurized fluid flows quickly or slowly, whether it fragments particles of vessel 12 and/or whether it changes its pressure. These noises are information concerning the state of vessel 12 and the effect of the pressurized fluid on the distal end section of the catheter. In similar fashion noises develop in the shaft 320 of catheter 302 of FIG. 2 and thus information as a function of the state of vessel 12 and the effect of tool 322 on the distal end section of the catheter. Preferred variants therefore consist of the fact that the sensor 114 of FIG. 1, the sensor 314 of FIG. 2 and the sensor 314 of FIG. 3 are noise or sound sensors and have means for optical and/or acoustic indication of information, preferably loudspeakers or earphones.

In all variants the information can be recorded and stored automatically in electronic or other means of storage.

What is claimed is:

1. An atherectomy apparatus, comprising:
   an elongate catheter having a distal end and a proximal end and a lumen therebetween;
   an atherectomy element distal the distal end of the catheter, wherein the atherectomy element operates by rotation;
   a shaft operably connected to the atherectomy element and extending through the lumen; and
   a measurement device for measuring changes in the atherectomy device; wherein the measurement device measures sound or the torque of the shaft.

2. The atherectomy apparatus of claim 1, wherein the measurement device measures the torque of the shaft.

3. The atherectomy apparatus of claim 2, wherein the measurement device comprises
   a first angle sensor disposed on the shaft;
   a second angle sensor disposed on the shaft; and
   a torsion spring disposed between and attached to the first and second angle sensors.

4. The atherectomy apparatus of claim 1, wherein the measurement device creates a plurality of data, and wherein the apparatus further comprises an output device to present the data in a human-understandable format.

5. The atherectomy apparatus of claim 4, wherein the output device comprises an acoustic signal generator that outputs the data as audible acoustic signals.

6. The atherectomy apparatus of claim 5, wherein the output device comprises an optical display element that outputs the data as displayable signals.

7. The atherectomy catheter of claim 1, wherein the measurement device is disposed at a proximal portion of the shaft.

8. The atherectomy catheter of claim 1, wherein the measurement device operates by measuring energy in the shaft that occurs as a function of the external effects in the environment of the rotational element.

9. The atherectomy apparatus of claim 1, wherein the measurement device senses sound waves in the shaft and wherein the measurement device is coupled to an output devices for making the sound waves audible.

10. The atherectomy apparatus of claim 1, wherein the measurement device measures sound waves generated by rotation of the atherectomy element.

11. An atherectomy apparatus, comprising:
- an elongate catheter having a distal end and a proximal end and a lumen therebetween;
- an atherectomy element distal the distal end of the catheter, the atherectomy element operating by rotation;
- a shaft operably connected to the atherectomy element and extending through the lumen; and
- a measurement device for measuring changes in the atherectomy device, the measurement device measuring the torque of the shaft, the measurement device including
- a first angle sensor disposed on the shaft;
- a second angle sensor disposed on the shaft; and
- a torsion spring disposed between and attached to the first and second angle sensors.

12. An atherectomy apparatus, comprising:

an elongate catheter having a distal end and a proximal end and a lumen therebetween;

an atherectomy element distal the distal end of the catheter;

a shaft operably connected to the atherectomy element and extending through the lumen; and a sensor for sensing changes in the atherectomy device, wherein the sensor senses sound waves in the shaft and wherein the sensor is coupled to an output devices for making the sound waves audible.

* * * * *